United States Patent
Sabin et al.

(10) Patent No.: US 10,258,353 B2
(45) Date of Patent: Apr. 16, 2019

(54) SURGICAL ASSEMBLY FOR THE IMPLANTATION OF AN IMPLANT IN AN OSSEOUS STRUCTURE

(71) Applicant: UBIPLUG, Saint-Contest (FR)

(72) Inventors: Pierre Sabin, Rouen (FR); Pierre-Yves Quelenn, Le Petit Quevilly (FR)

(73) Assignee: UBIPLUG (FR)

( * ) Notice: Subject to any disclaimer, the term of this patent is extended or adjusted under 35 U.S.C. 154(b) by 83 days.

(21) Appl. No.: 15/108,722

(22) PCT Filed: Dec. 23, 2014

(86) PCT No.: PCT/IB2014/003119
§ 371 (c)(1),
(2) Date: Jun. 28, 2016

(87) PCT Pub. No.: WO2015/097555
PCT Pub. Date: Jul. 2, 2015

(65) Prior Publication Data
US 2016/0354094 A1  Dec. 8, 2016

Related U.S. Application Data (60) Provisional application No. 61/920,724, filed on Dec. 24, 2013.

(51) Int. Cl.
*A61B 17/16* (2006.01)
*A61B 17/17* (2006.01)

(52) U.S. Cl.
CPC ...... *A61B 17/1739* (2013.01); *A61B 17/1695* (2013.01); *A61B 2217/005* (2013.01)

(58) Field of Classification Search
CPC ............ A61B 17/1695; A61B 17/1739; A61F 2/2875
See application file for complete search history.

(56) References Cited

U.S. PATENT DOCUMENTS

| | | | |
|---|---|---|---|
| 5,263,939 A * | 11/1993 | Wortrich | A61B 17/34 128/DIG. 26 |
| 5,743,916 A | 4/1998 | Greenberg et al. | |
| 6,752,812 B1 * | 6/2004 | Truwit | A61B 90/11 606/1 |

(Continued)

FOREIGN PATENT DOCUMENTS

WO  2014001501 A2  1/2014

OTHER PUBLICATIONS

International Search Report for Application No. PCT/IB2014/003119 dated Apr. 22, 2015, 2 pages.

*Primary Examiner* — Nicholas W Woodall
(74) *Attorney, Agent, or Firm* — Lerner, David, Littenberg, Krumholz & Mentlik, LLP (57) ABSTRACT

The invention relates to a surgical assembly for the implantation of an implantable device in a cavity formed in an osseous structure, comprising abase template intended to be fixed to the osseous structure and a plurality of interchangeable templates intended to be successively coupled to the base template, each of the interchangeable templates having at least one through opening to be used for guiding of a tool to form the cavity in the osseous structure and/or position of the implantable device into the cavity.

17 Claims, 6 Drawing Sheets

(56) References Cited

U.S. PATENT DOCUMENTS

| | | | |
|---|---|---|---|
| 6,913,463 B2 * | 7/2005 | Blacklock | A61B 17/176 408/115 R |
| 9,009,012 B2 * | 4/2015 | Bake | A61F 2/30756 703/6 |
| 2009/0118736 A1 | 5/2009 | Kreuzer | |
| 2011/0106093 A1 | 5/2011 | Romano et al. | |

* cited by examiner

SURGICAL ASSEMBLY FOR THE IMPLANTATION OF AN IMPLANT IN AN OSSEOUS STRUCTURE

CROSS REFERENCE TO RELATED APPLICATIONS

The present application is a national phase entry under 35 U.S.C. § 371 of International Application No. PCT/IB2014/003119, filed Dec. 23, 2014, published in English, which claims priority from U.S. Provisional Patent Application No. 61/920,724 filed Dec. 24, 2013, all of which are incorporated herein by reference.

FIELD OF THE INVENTION

The invention relates to a surgical assembly for the implantation of an implantable device in a cavity formed in an osseous structure, in particular to implant a medical device preferably composed of several parts in the bone skull of a patient, the patient being a human or being an animal.

TECHNICAL BACKGROUND

In the recent years, new generations of implantable devices have been developed intended to be implanted in an osseous structure of a patient, those implantable devices having more and more complex shapes, and being of relatively large dimensions, thus making the implantation process more and more difficult, from the preparation of the osseous structure to the implantation of the device itself.

For instance, it has been recently proposed new shapes of permanent percutaneous connection device to be implanted in an osseous structure of a patient, and used for instance to connect a medical apparatus implanted in the body of the patient with a device external to the patient, preferably for transfer of energy and/or of matter, such as fluids.

Examples of such specific implantable devices are described in more detail in the international application published under the reference WO 2014/001501 on Jan. 3, 2014.

The difficulties reside in the preparation of the osseous structure to form a cavity which is dimensioned to receive the implantable device having large and specific dimensions. The processing of the osseous structure must indeed be as simple as possible for the surgeon who has to implant the implantable device, but also as smooth as possible with regard to the osseous structure itself, in order to preserve the bone integrity for instance.

The proper positioning of those new implantable devices can also lead to some difficulties for the surgeon, in particular because those devices have complex shapes and/or are made of several parts that are to be assembled together when being implanted in the cavity made in the osseous structure or the patient.

In the above-mentioned international application WO 2014/001501, there is for instance proposed a percutaneous connection device to be implanted within a cavity formed in the skull of a patient, comprising:
 a percutaneous socket having a first end comprising a percutaneous abutment and a second end opposite to the first end designed to be anchored by osseointegration within the cavity made in the osseous structure of the patient; and
 an elongated extension member designed to be inserted within a hole created into the osseous structure, said extension member having a first end comprising means to be removably coupled to the second end of the socket, and a second end opposite to the first end, the removable coupling of the extension member relative to the percutaneous socket being designed for angular shifting of the first end of the percutaneous socket relative to the second end of the extension member.

A first challenge for such implantable percutaneous connection device is thus to create the cavity intended to receive the main body of the device, and further process the osseous structure so that it can also receive the other structural elements forming the implantable device.

Another challenge resides in the relative positioning of the different structural elements forming the implantable device, which has to be very accurate so that the implantable device can be implanted properly and can be also operated properly.

A goal of the present invention is thus to propose a new surgical assembly for the implantation of an implantable device in a cavity formed in an osseous structure that solves at least one of the above-mentioned problems.

More specifically a goal of the present invention is to propose a new surgical assembly used to implant a device and to position or connect perfectly another device or system implanted in the bone thickness.

Another goal of the present invention is to propose a surgical assembly enabling the creation of a cavity in an osseous structure of a patient while preserving the surrounding bone integrity and potentially the biological characteristics of the bone.

Still another goal of the invention is to propose a surgical assembly for the implantation of an implantable device in a cavity formed in an osseous structure which eases the surgical procedure performed by the surgeon, in particular with regard to the creation of the cavity itself and/or the positioning of the implantable device in the cavity.

SUMMARY OF THE INVENTION

To this end, there is provided a surgical assembly as defined in the appended claims.

In particular, there is provided a surgical assembly for the implantation of an implantable device in a cavity formed in an osseous structure, comprising a base template intended to be fixed to the osseous structure and a plurality of interchangeable templates intended to be successively coupled to the base template, each of the interchangeable templates having at least one through opening to be used for guiding of a tool to form the cavity in the osseous structure and/or position of the implantable device into the cavity, wherein the base template comprises a receiving portion for the coupling of each one of the plurality of interchangeable templates to the base template, said receiving portion having a reference surface for specifically positioning each one of the plurality of interchangeable templates relative to the base template, and
wherein the assembly further comprises a retaining element to securely fasten each of the plurality of interchangeable templates relative to the base template.

Preferable but not limited aspects of such surgical assembly, taken alone or in any possible technical combination, are the following:
 the plurality of interchangeable templates comprises at least one drilling template having at least one through drilling opening to be used for guiding of a drilling tool to form the cavity in the osseous structure.

the drilling template comprises a plurality of drilling openings, at least two of the drilling openings being arranged with an overlap to one another.

the drilling template comprises a drilling opening having a cylindrical shape with dimensions fit to guide a drilling bur, preferably a standard drilling bur.

the plurality of interchangeable templates comprises at least one implantation template having at least a through implantation opening shaped for guiding the positioning of the implantable device into the cavity.

the surgical assembly further comprises an implanting tool intended to be used for implanting the implantable device in the cavity with the guiding of the implantation opening.

the implanting tool comprises a first part comprising a lever for rotating the implanting tool, and a second part coupled to the first part at a first end and coupled to the implantation template on an other end, wherein the couplings are designed so that a rotation of the lever imparts a translation movement and/or a rotation movement of the implantable device.

the implantation template further comprises at least one through drilling opening to be used for guiding of a drilling tool to form a further hole in the osseous structure, said drilling opening being non-parallel to the implantation opening and arranged so that the hole can be drilled up to the cavity.

the implantation template further comprises a locking element intended to cooperate with a corresponding recess provided in the implantable device to secure the positioning of the implantable device relative to the implantation template.

at least one of the interchangeable templates comprises a reference protrusion intended to cooperate with a surface of the cavity formed in the osseous structure to further secure positioning of said interchangeable template relative to the base template fixed in the osseous structure.

at least one of the interchangeable templates comprises at least one complementary through opening for evacuation of osseous chips being formed upon drilling of the osseous structure.

the base template has a groove for receiving the retaining element, the retaining element has a protruding portion and each of the plurality of interchangeable templates comprises a recess, said protruding portion being insertable within the recess of any interchangeable template been positioned in the receiving portion of the base template in order to lock said interchangeable template relative to the base template.

the retaining element comprises an arc member rotatively coupled to a cylindrical portion of the base template.

the base template comprises an evacuation opening provided through the reference surface of the receiving portion, said evacuation opening being preferably larger than the through opening of the interchangeable templates to ease evacuation of osseous chips being formed upon drilling of the osseous structure.

the receiving portion of the base template comprises a cylindrical portion with a flat ring arranged at one end of said cylindrical portion to form the reference surface, and wherein the interchangeable templates comprises a cylindrical portion having dimensions to closely fit the dimensions of the cylindrical portion of the receiving portion in order to be positioned therein.

the interchangeable templates further comprises an elongated portion protruding from the cylindrical portion of the interchangeable template, and wherein the cylindrical portion of the receiving portion of the base template comprises a lateral opening to receive said elongated portion of the interchangeable template.

the surgical assembly further comprises a drilling tool having at least a drilling bur, wherein said drilling bur comprises a stop element provided at a specific position along its elongated axis so as to mechanically limit penetration of the drilling bur into the osseous structure.

DESCRIPTION OF THE FIGURES

Other characteristics and advantages of the invention will become clear from the following description which is only given for illustrative purposes and is in no way limitative and should be read with reference to the attached drawings on which.

DETAILED DESCRIPTION OF THE INVENTION

The surgical apparatus which is proposed for the implantation of an implantable device in a cavity formed in an osseous structure is an assembly composed of several elements used successively in order to create progressively bone holes or cavity, and in order to implant an implantable device 301 that may be composed of several parts (301a, 301b).

Such implantable device can be for instance one percutaneous connection device as described in the international application WO 2014/001501 which is hereby entirely incorporated by reference.

Figure 13:
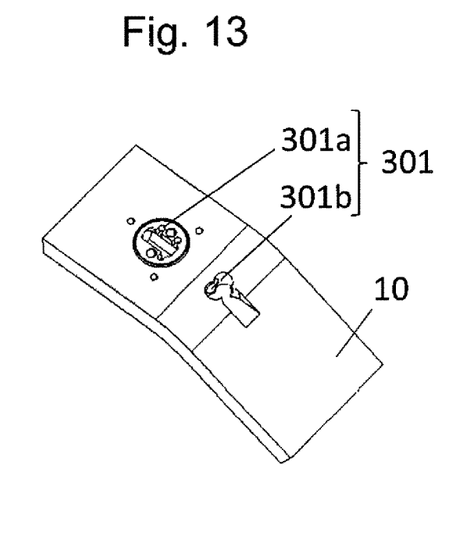

FIG. 13 illustrates an example of such implantable device 301 being implanted in an osseous structure 10, here a schematic calvaria 10, comprising a main implant body 301a preferably comprising the percutaneous abutment, and a removable elongated extension member 301b.

The proposed surgical assembly for the implantation of an implantable device in a cavity formed in an osseous structure, thus preferably comprises a base template 501 intended to be fixed to the osseous structure and a plurality of interchangeable templates (502, 503, 504, 505) intended to be successively coupled to the base template 501.

Each of the interchangeable templates has at least one through opening to be used for guiding of a device to form the cavity in the osseous structure and/or position of the implantable device 301 into the cavity.

The base template 501 comprises a receiving portion 510 for the coupling of each one of the plurality of interchangeable templates to the base template 501. Preferably, the receiving portion 510 of the base template 501 is designed to receive a single interchangeable template at a time. As will be described in more details below, the principle of the invention is indeed to provide a base template 501 that is used as a reference for the creation of the cavity and/or the positioning of the implantable device. The interchangeable templates are thus used successively depending on the operation the surgeon wants to do with the osseous structure, e.g. either drilling or implanting.

Once the intended location of the implant device 301 has been spotted on the osseous structure, e.g. the skull, the base template 501 is fixed on the skull.

Such primary positioning of the base template 501 on the osseous structure is for example done by use of pre-operative images taken to determine the exact position where the implantable device 301 has to be placed, and thus infer where the base template 501 shall be positioned to create the cavity in the osseous structure and/or position the implantable device.

The base template 501 may be fixed to the osseous structure by any fixation means. For instance, it may be screwed on the bone by one or several osteosynthesis screws 520, or secured on a preexisting device or nailed or fixed by another way. In a particular embodiment, the base template 501 is fixed at the surface of the bone by three osteosynthesis screws 520.

The base template 501 is designed to support other modular elements, i.e. interchangeable templates to perform the procedure.

The receiving portion 510 is formed so as to provide a reference surface 511 for specifically positioning each one of the plurality of interchangeable templates relative to the base template 501.

The receiving portion 510 has thus a reference surface 511 and all the interchangeable templates are positioned according to this reference surface 511.

Using a base template 501 with a reference surface that can receive all the interchangeable templates that the surgeon will need for the procedure is very advantageous as this enable the proceedings not to depend on the specific feature of the patient. In particular, as the reference is the same single element for every patient (i.e. the base template), the use of the template during the proceedings will be the same for all the patients. The only specific step is thus only the fixation of the base template.

In the embodiment described above with a fixation by screws, the base template 501 is designed so that the screws are placed upon a flange in a way that the heads of the screws do not modify the reference surface 511 of the template 501.

The reference surface 511 is preferably planar but can have other configurations.

Advantageously, the reference surface 511 is designed so that it provide a large surface of contact with the interchangeable templates, which creates a large support area for the interchangeable templates and thus enables spreading the stress transmitted from the interchangeable template to the osseous structure when the surgeon is preparing the cavity and/or positioning the implantable device.

The more points of contact between the interchangeable templates and the osseous structure (or base template fixed on the osseous structure) and/or the larger the support area, the less stress will be transmitted to the osseous structure at a specific point. This reduces the risks of damaging the osseous structure.

In a first embodiment as illustrated in the figures, the base template 501 has a circular shape with an opening on one side.

Preferably, the receiving portion 510 of the base template 501 comprises a cylindrical portion with a flat ring arranged at one end of said cylindrical portion to form the reference surface 511. In such case, the interchangeable templates preferably comprises a cylindrical portion 531 having dimensions to closely fit the dimensions of the cylindrical portion of the receiving portion 510 in order to be positioned therein.

Even more preferably, the interchangeable templates further comprises an elongated portion 532 protruding from the cylindrical portion 531 of the interchangeable template, and the cylindrical portion of the receiving portion 510 of the base template 501 comprises a lateral opening 533 to receive said elongated portion 532 of the interchangeable template.

The base template 501 is preferably made in a biocompatible metallic matter or in another biocompatible material. Preferably, the interchangeable templates are also made in a biocompatible material.

The bottom of the base template 501 is preferably largely carved in order to facilitate the bone chips evacuation and the irrigation flow when holes are made.

For instance, the base template 501 comprises an evacuation opening provided through the reference surface 511 of the receiving portion 510, said evacuation opening being larger than the through opening of the interchangeable templates to ease evacuation of osseous chips being formed upon drilling of the osseous structure.

The surgical assembly further comprises retaining means to securely fasten each of the plurality of interchangeable templates relative to the base template 501.

In order to fix modular elements, i.e. the interchangeable templates, on the base template, the retaining means can be a mechanical retaining element (512). The mechanical retaining element can be monobloc or distinct from the base template 501.

The base template 501 has for instance a groove for receiving the retaining element 512, the retaining element being designed to have a portion protruding from the groove inside the receiving portion.

Each of the plurality of interchangeable templates preferably comprises a recess 534, said protruding portion being insertable within the recess 534 of any interchangeable template been positioned in the receiving portion 510 of the base template 501 in order to lock said interchangeable template relative to the base template 501.

Figure 17:
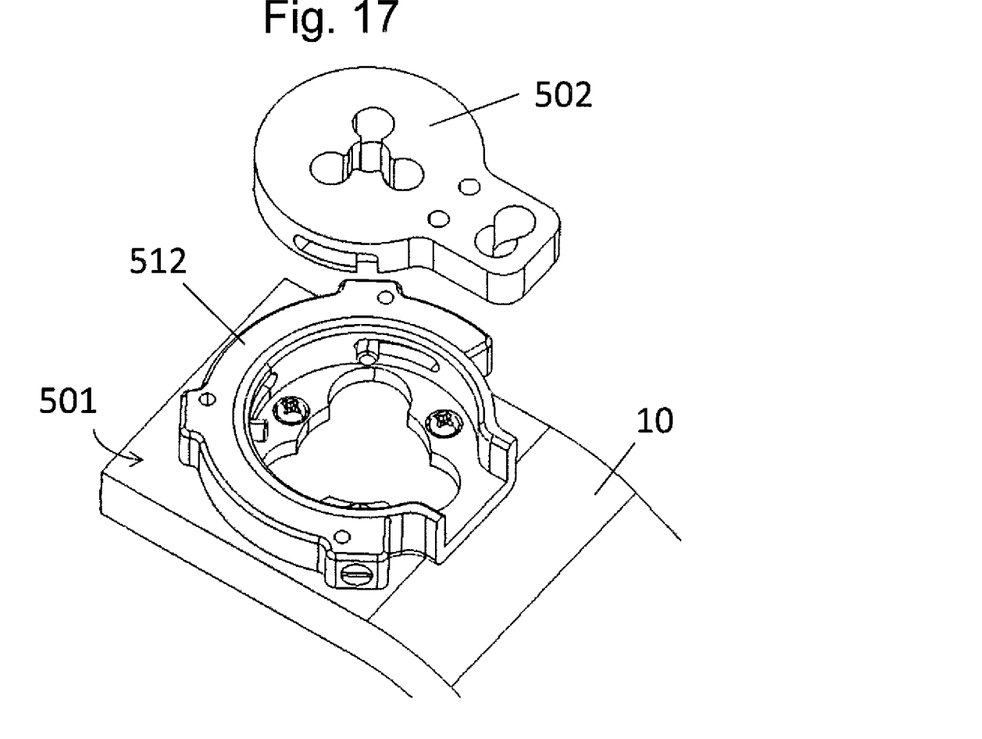
FIG. 17 illustrates a surgical assembly according to the first embodiment of the invention, with a retaining element coupled to the base template in an unlocked position to receive an interchangeable template.
Figure 18:
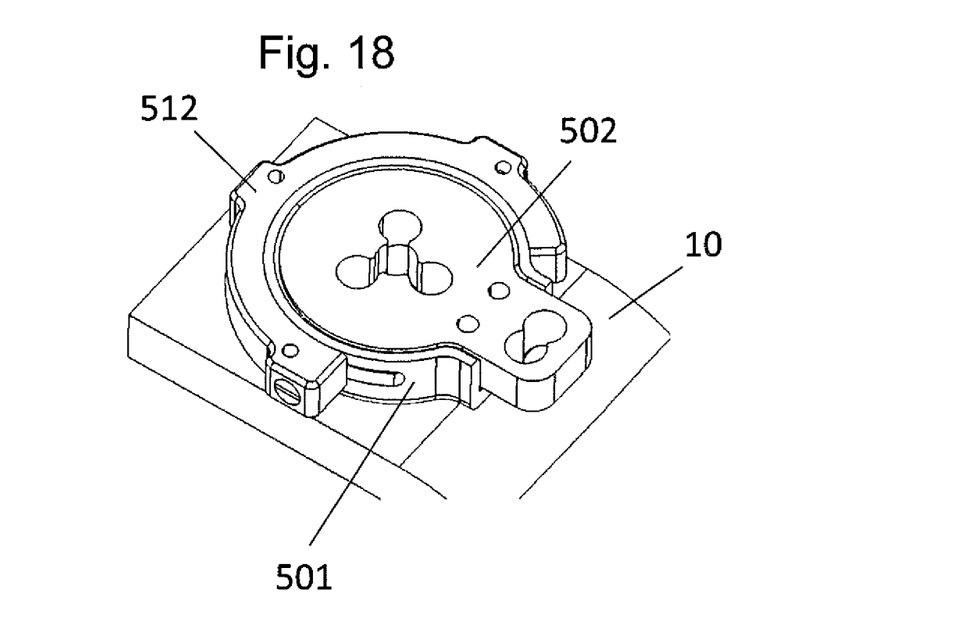
FIG. 18 illustrates the surgical assembly of FIG. 17 where the retaining element is in a locked position securely fasten the interchangeable template to the base template.

In the embodiment illustrated through FIGS. 1 to 12, which is illustrated in more details on FIGS. 17 and 18, the retaining element 512 is mounted on the base template 501. Such retaining element 512 comprises an arc member rotatively coupled to a cylindrical portion of the base template. Such arc member can be considered as a partial ring mounted on the base template 501.

On FIG. 17, the arc member 512 is in an unlocked position where the interchangeable template 502 can be freely inserted on and removed from the base template 501.

On FIG. 18, the arc member 512 is in a locked position where the interchangeable template 502 is securely fastened to the base template 501, and cannot be removed without rotating the arc member 512 relative to the base template 501.

Figure 19:
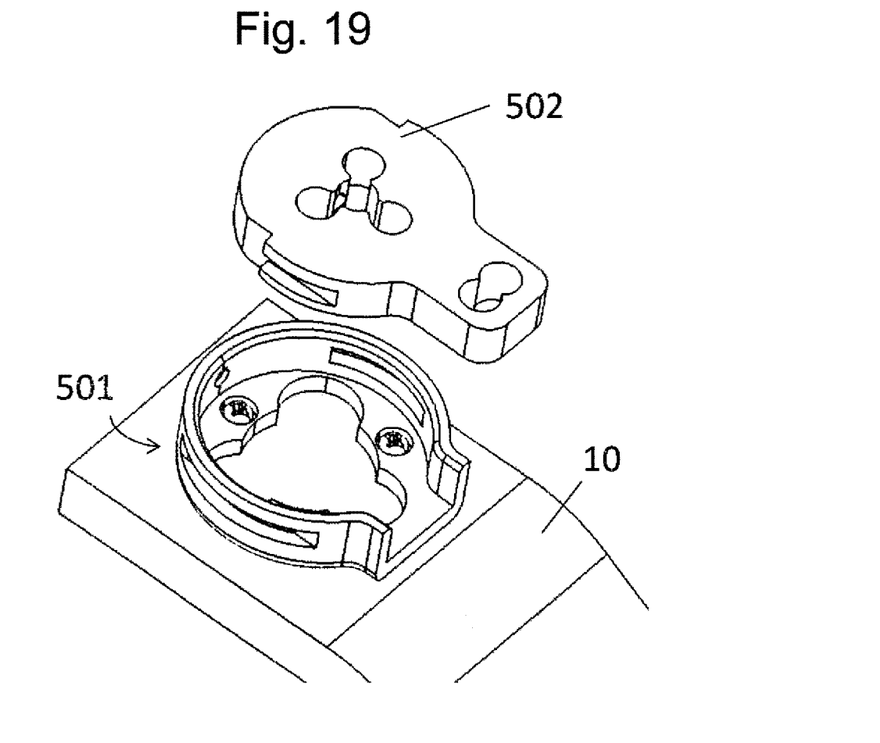
FIG. 19 illustrates a surgical assembly according to a second embodiment of the invention, with a base template adapted to receive a removable retaining element.
Figure 20:
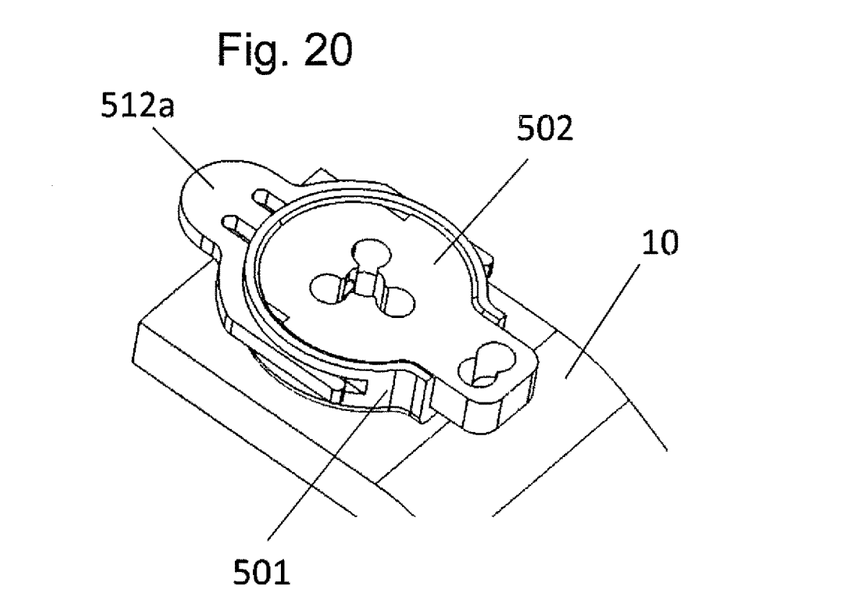
FIG. 20 illustrates the surgical assembly of FIG. 19 where the retaining element is securely fasten the interchangeable template and the base template.

FIGS. 19 and 20 illustrate another embodiment of the assembly, where the retaining element 512a is a separate element that is designed to be translated within the groove arranged in the base template 501.

In such embodiment, the retaining element 512a has for example the shape of a fork having three arms that are designed to protrude within the receiving portion 510 of the base template 501.

As mentioned above, several modular elements, so called interchangeable templates, are successively placed on the base template in order to firstly create the cavity where the implantable device has to be positioned.

To this end, the plurality of interchangeable templates preferably comprises at least one drilling template, and most preferably several drilling templates (502, 503, 504). A drilling template has the specificity of having at least one through drilling opening 535 to be used for guiding of a drilling tool to form the cavity in the osseous structure.

The use of the drilling openings 535 enables to precisely drill some holes of a desired diameter in the bone.

In order to preserve the bone integrity and avoid overheating it, the drilling is preferably done progressively with a limited rotation speed of the drilling tool.

The drilling templates (502, 503, 504) are preferably arranged with drilling openings shaped after a specific cylindrical dimension corresponding to a specific size of a bur used in the drilling tool.

Providing several drilling templates, where each drilling template comprises one or several drilling opening 535 arranged in a specific way, enables the use of a single bur to drill a large bone zone in a limited time. This further enables creating several different cavities in the osseous structure as will be apparent from the description below.

Preferably a drilling template comprises a drilling opening having a cylindrical shape with dimensions fit to guide a drilling bur, preferably a standard drilling bur.

By "standard drilling bur" is understood a bur having a diameter usually used in the field of implantology, i.e. drilling bur with a section having a diameter of between 1 mm and 5.5 mm, preferably of 4 mm.

Using such drilling opening as a guide for the drilling is very advantageous as this eases the gesture of the surgeon and enables him to create precise holes without having to exercise to much effort. This guide also avoids any possible offset of the bur while drilling the osseous structure as it ensures that the bur remains in the required drilling direction.

In a preferred embodiment, there are used standard burs in respect of their diameter, which are however adapted and specifically designed to assist the surgeon while he is drilling the holes in the osseous structure.

In particular, a graduation can be marked along the bur giving the surgeon indications as to the depth of penetration of the bur into the osseous structure.

Alternatively or additionally, the bur can comprise a stop element that mechanically limits the possible translation of the bur into the drilling opening, and thus limits the depth of the drilling. Such stop element can for instance be a ring surrounding the bur at a distance from the free end of the bur chosen according to the required depth for the hole.

These elements that may be provided on the bur are very advantageous in that they further ease the work of the surgeon, and increase the safety of the surgical procedure. In particular, this prevent the surgeon from drilling too deeply and possibly pass through the osseous structure and thus damage what is located on the other side of the osseous structure. When the cavity is to be done in the calvaria for instance, this prevents any risk of drilling through the dura-matter.

Preferably each drilling template comprises a plurality of drilling openings 535. The drilling openings are arranged on the drilling template depending on the cavity to be formed in the osseous structures.

The drilling openings 535 can be arranged with overlaps or with gaps.

Figure 15:
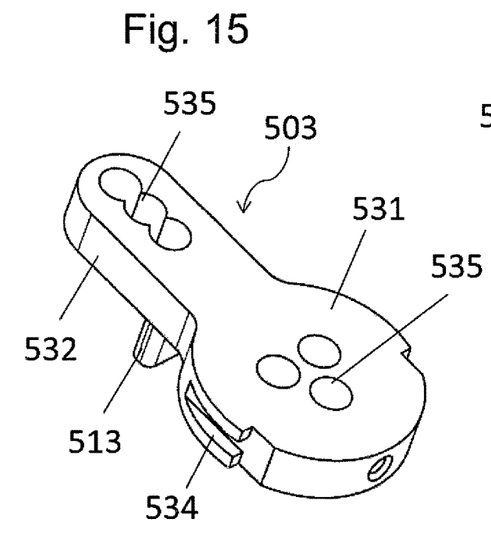
FIG. 15 is a perspective view illustrating a first embodiment of a drilling template of a surgical assembly according to the invention.

For example, in the drilling template 503 illustrated in FIG. 15, there are three drilling openings 535 arranged in the elongated portion 532 with an overlap to one another, three drilling openings 535 arranged in the cylindrical portion 531 with gaps, i.e. without overlapping to one another.

Figure 16:
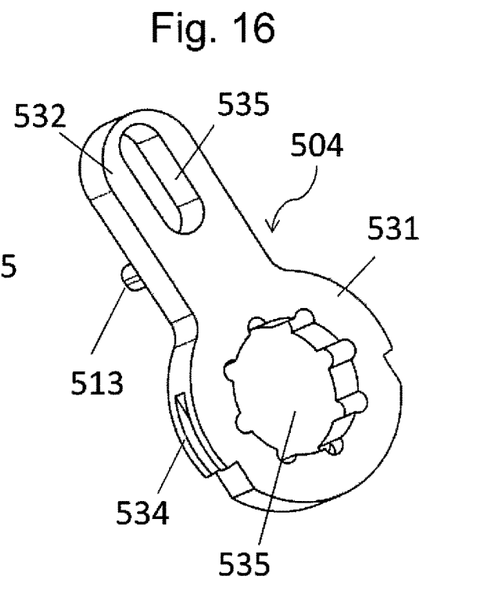
FIG. 16 is a perspective view illustrating a second embodiment of a drilling template of a surgical assembly according to the invention.

In the embodiment of the drilling template 504 illustrated in FIG. 16, the drilling openings 535 provided in the elongated portion 532 overlap to one another, as well as the drilling openings 535 provided in the cylindrical portion 531.

Depending on the cavity to be formed in the osseous structure, one or several drilling templates (502, 503, 504) may be placed on the base template 501 and preferably secured by a mechanical retaining element 512 before the surgeon starts drilling the bone to form holes in a view of forming the cavity.

Depending on the bone curve, bone removal can be realized in a localized zone in order to create an approach to drill into the bone thickness. These holes can be through holes or blind holes.

When drilling one or several holes distant from the reference surface of the base template (from 10-15 mm), one or several additional reference surface on the bone may be created in order to further limit the mechanical stress on the base template.

The interchangeable templates may thus comprise a reference protrusion 513 intended to cooperate with such reference surface formed in the osseous structure. In addition to relieving the overall mechanical stress on the base template, this also further secures the positioning of the interchangeable template relative to the base template 501 fixed in the osseous structure 10. In particular, the mechanical element 513 in the form of a reference protrusion for instance, will lay on this additional reference surface made in the osseous structure.

The holes in the bone permit to implant one or several devices. When the cavity has been created in the osseous structure of the patient, the implantable device has to be positioned and implanted properly.

To this end, the plurality of interchangeable templates preferably comprises at least one implantation template 505 having at least a through implantation opening 536 shaped for guiding the positioning of the implantable device 301 into the cavity.

The implantation template 505 is used to facilitate the implantation of the implantable device 301 according to a specific orientation.

Figure 14:
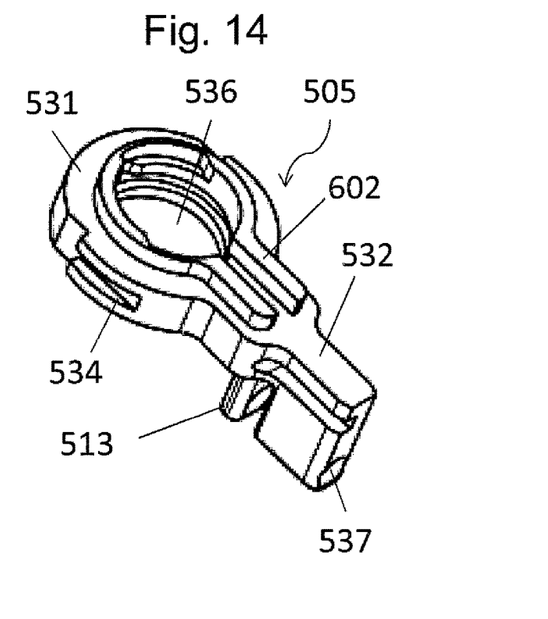
FIG. 14 is a perspective view illustrating an embodiment of an implantation template of a surgical assembly according to the invention.

Preferably as illustrated on FIG. 14, the implantation template 505 comprises an implant holder 602, which has a shape adapted to receive the main body of the implant device

301a to be positioned and that cooperates with the implantation opening 536 to ease the alignment and positioning of the implant device 301a. The implant holder 602 may be assembled with the implantation template (505) with a specific orientation and depth.

In an advantageous embodiment, the implantation template 505 further comprises at least one through drilling opening 537 to be used for guiding of a drilling tool to form a further hole in the osseous structure. Preferably, this drilling opening 537 is non-parallel to the implantation opening and arranged so that the hole can be drilled up to the cavity, i.e. in order to join the cavity.

In this case, the implantation template 505 may also be used to drill one or several holes in the bone. This newly created hole may be required to receive one or several other parts (301a, 301b) forming the implantable device 301.

The implantation template 505 may thus enable to assemble or connect two or several implantable parts (301a, 301b) in a specific orientation.

As mentioned above, the drilling opening 537 of the implantation template 505 eases the work of the surgeon to form the holes necessary for the implantation of the implantable device 301, and secure the procedure as it avoids any offset during the drilling.

The implant holder 602 may have a specific handle mean associated to the anchoring means of the implanted device. An implanting tool 601 can thus be used for implanting the implantable device 301 in the cavity with the guiding of the implantation opening 536.

In one specific embodiment, a crank 601 can be used to implant a screwed implant. Such crank is used for both translating the implant 301 into the cavity formed in the osseous structure and to rotate such implant 301 within the cavity, which enables securing the implant 301 to the osseous structure should the implant comprise adapted anchoring means.

Figure 21:
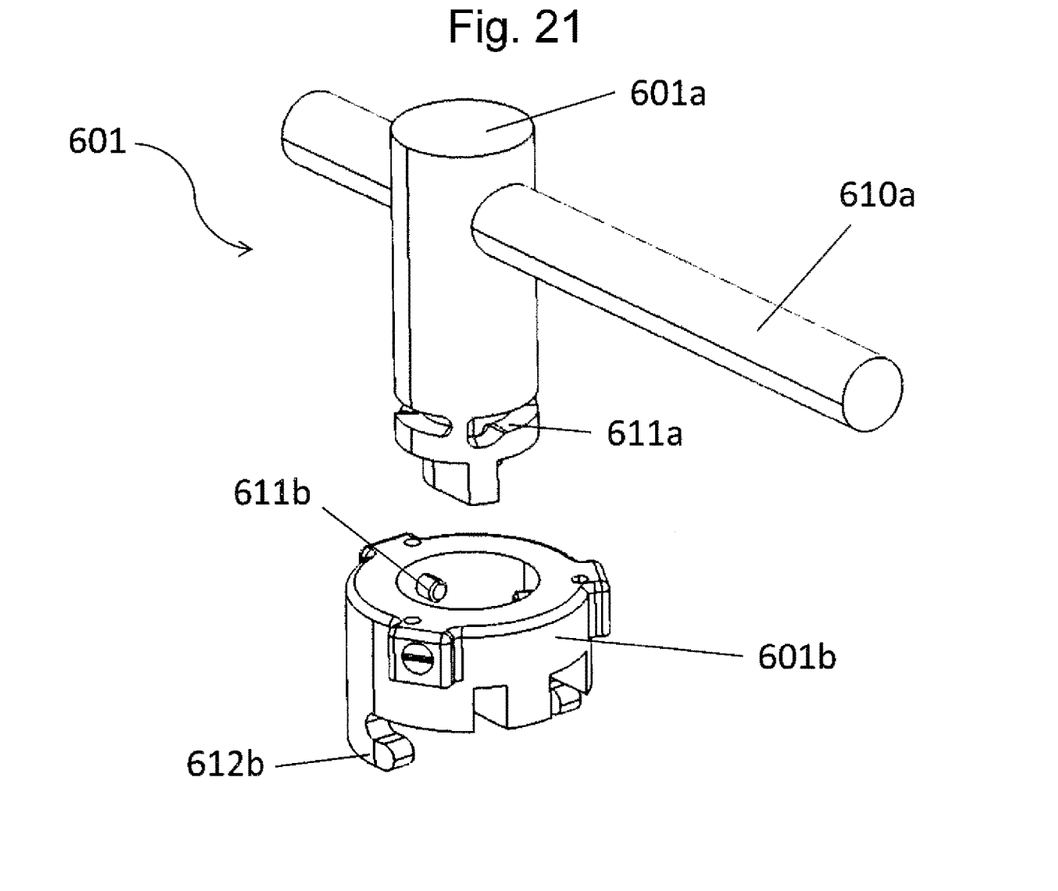
FIG. 21 illustrates an implanting tool to be used in the surgical assembly of the invention.

An example of such implanting tool 601 is illustrated on FIG. 21. According to this embodiment, the implanting tool 601 comprises a first part 601a that comprises a lever 610a to impart a movement of rotation, and a second part 601b which is connected on one end to the first part 601a and on the other end with the implantable device 301 to be implanted.

The coupling between the first part 601a and the second part 601b can be made to transform the movement of rotation of the lever into another movement to impart to the implantable device.

In the example illustrated on FIG. 14, the coupling is made by the cooperation of a protrusion 611b made on the second part 601b with a groove 611a arranged on the first part 601a with specific dimensions.

Preferably the second part 601b of the implanting tool 601 has also a specific protruding element 612b provided for coupling of the tool 601 with the implant holder 602 and implantation element 505. For instance the coupling is designed so that there is only one angular position where the implanting tool 601 is unlocked from the implant holder 602 and implantation element 505 (see FIG. 10) whereas it remains in a locked position for all other angular positions (see for instance FIG. 9).

According to another preferred embodiment, the implantation template 505 may further comprise a locking element 603 intended to cooperate with a corresponding recess provided in the implantable device to secure the positioning of the implantable device relative to the implantation template.

FIGS. 1 to 13 illustrate an example of use of a surgical assembly as described, in order to prepare the bone structure for receiving an implantable device as described in WO 2014/001501, and the further steps of positioning and implanting the parts forming such implantable device.

Figure 1:
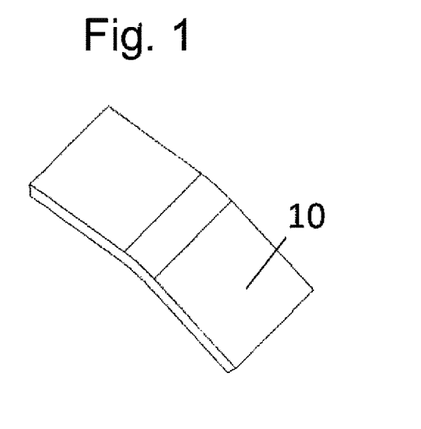
FIGS. 1 to 13 illustrate the use of a surgical assembly according to a first embodiment of the invention, for the creation of a cavity in an osseous structure and the implantation of an implantable device in such cavity.

On these figures, FIG. 1 represents a schematic partial calvaria 10 before any drilling of holes.

Figure 2:
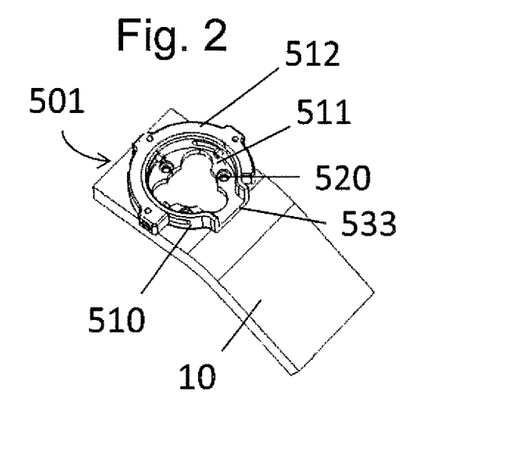

The first step of the procedure as illustrated in FIG. 2 consists in positioning the base template 501 on the surface of the osseous structure 10, and securely fixing such base templates 501 on the calvaria 10 by way of osteosynthesis screws 520 for example.

Figure 3:
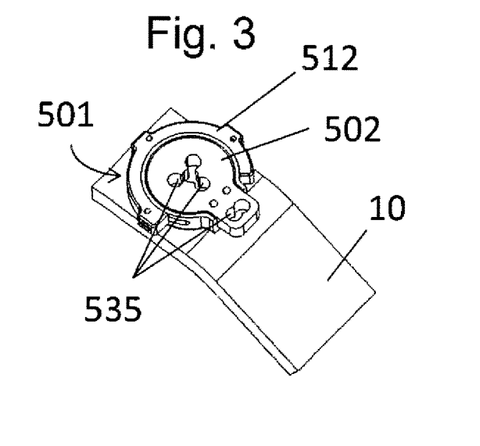

In a second step as illustrated in FIG. 3, a first drilling template 502 is positioned in the receiving portion of the base template 510, and securely fastens to it with the retaining arc member 512. Holes are then drilled in the osseous structure 10 by using the several drilling openings 535 of the first drilling template 502.

Figure 4:
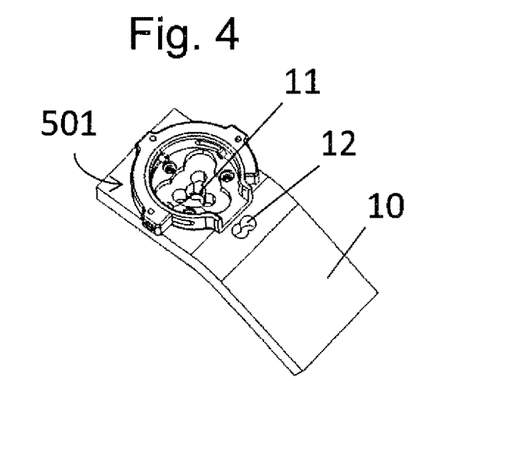

After the holes corresponding to the drilling openings 535 of the first drilling template 502 have been formed, the first drilling template 502 is removed from the base template 501. As illustrated in FIG. 4, the osseous structure thus comprises a first cavity 11 and a second cavity 12, which have been respectively done with the drilling openings of the cylindrical portion 531 of the first drilling template 502 and with the drilling openings of the elongated portion 532 of the first drilling template 502.

It has to be noted that in this example, the second cavity 12 has a surface that will serve as a reference surface for the further interchangeable templates (503, 504, 505) which all include a reference protrusion 513 to increase their support area and thus reduce the mechanicals stresses.

Figure 5:
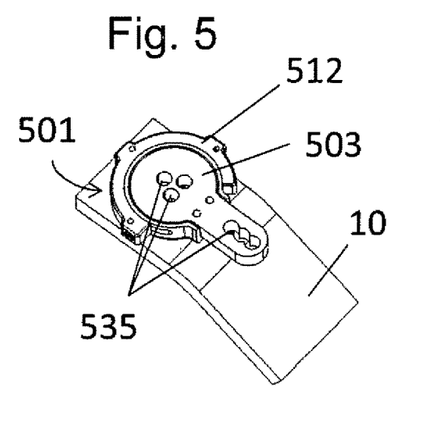

In a third step as illustrated in FIG. 5, a second drilling template 503 is positioned in the receiving portion of the base template 510, and securely fastens to it with the retaining arc member 512. Holes are then drilled in the osseous structure 10 by using the several drilling openings 535 of the second drilling template 503.

Figure 6:
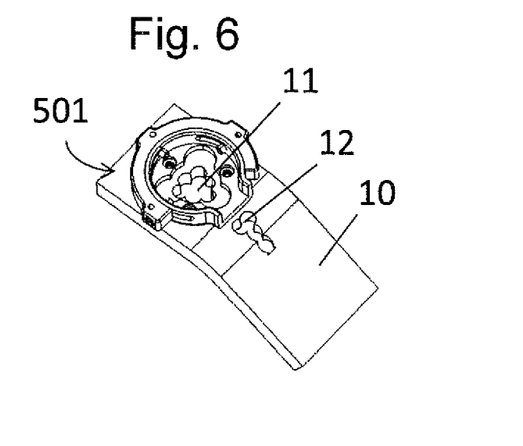

After the holes corresponding to the drilling openings 535 of the second drilling template 503 have been formed, the second drilling template 503 is removed from the base template 501. As illustrated in FIG. 6, the osseous structure thus comprises a first cavity 11 and a second cavity 12, those cavities having shape different from the respective first cavity 11 and a second cavity 12 made after having used the first drilling template 502.

Figure 7:
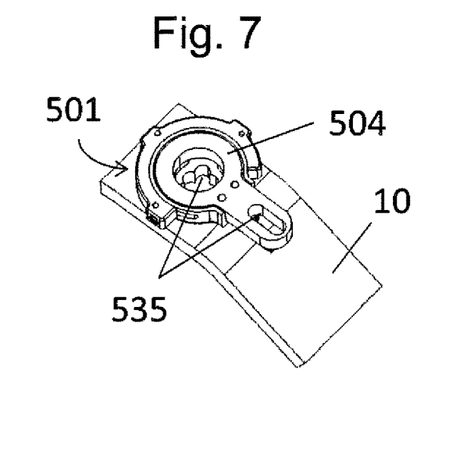

In a fourth step as illustrated in FIG. 7, a third drilling template 504 is positioned in the receiving portion of the base template 510, and securely fastens to it with the retaining arc member 512. Holes are then drilled in the osseous structure 10 by using the several drilling openings 535 of the third drilling template 504.

Figure 8:
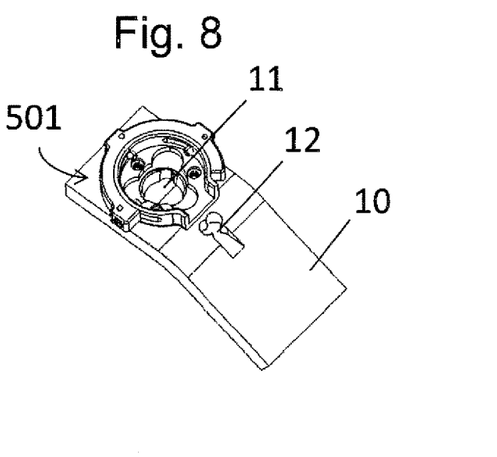

After the holes corresponding to the drilling openings 535 of the third drilling template 504 have been formed, the third drilling template 504 is removed from the base template 501. As illustrated in FIG. 8, the osseous structure thus comprises a first cavity 11 and a second cavity 12, those cavities having shape different from the respective first cavity 11 and a second cavity 12 made after having used both the first and second drilling templates (502, 503).

These successive steps of drilling have enabled forming two cavities (11, 12) in the osseous structure 10, that will be used to position and implant the implantable device 301, which in this example comprises a main implant part 301a and an elongated extension member 301b.

As is apparent from FIGS. 4, 6 and 8, the first and second cavities have a shape whose dimensions evolve after the different drilling steps. The second and third steps aimed at drilling several successive holes, each hole having a relatively small diameter to avoid over-heating of the osseous structure, such that the combination of all these holes that partially overlap forms the general shape of the first and second cavities.

The fourth step is a final drilling to create the first and second cavities of the required shape. The drilling bur that is used has a larger diameter than the one used in the second and third steps, but as most of the osseous material has already been removed, the drilling can be done quickly, without over-heating the osseous structure.

The first cavity that has been drilled has a shape that substantially corresponds to the external shape of the implantable device. In particular, the first cavity may have the global shape of a cylinder with further recesses having been formed, in the shape of hears. Those recesses are preferably provided to fit the shape of the anchoring elements that may be arranged on the side of the implantable part having a substantially cylindrical shape.

Figure 9:
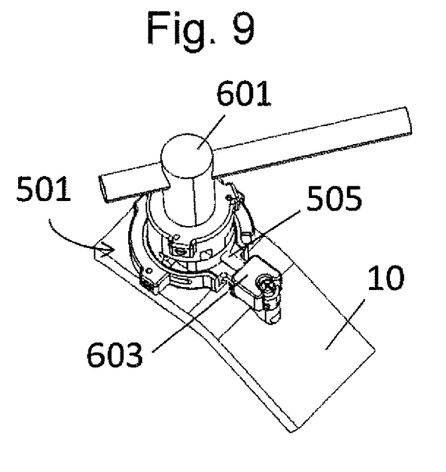
Figure 10:
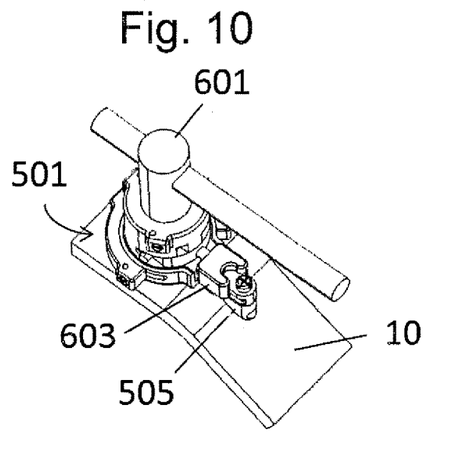

In the following fifth step of the procedure, as illustrated in FIG. 9, an implantation template 505 is positioned in the receiving portion of the base template 510, and securely fastens to it with the retaining arc member 512. In this embodiment, the main implant part 301a of the implantable device 301 is already positioned on the implantation template 505 as well as the implanting tool 601 which is coupled to the main implant part 301a.

The implanting tool 601 is then used to first translate the main implant part 301a into the first cavity 11 and secondly rotate said main implant part 301a around its axis of revolution. Preferably, the main implant part 301a has anchoring means designed to anchor the main implant part 301a into the osseous structure upon rotation. The implanting tool is rotated until it reaches a stop which means that the main implant 301a has reached its required position, and which corresponds to the unlocked position of the implanting tool 601 where the implanting tool 601 can be removed from the implantation template 505.

Figure 11:
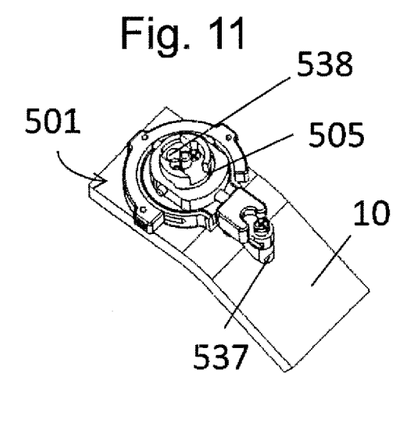

In a seventh step as illustrated in FIG. 11, a tangential hole is drilled through the drilling opening 537 of the implantation template 505.

In this step, it is preferable that the implanting tool 601 is removed from the implantation template 505 so that an access to the first cavity is possible through the interior cavity of the main implant part 301a for instance.

According to a specific embodiment, the base template 505 comprises an evacuation opening 538 provided through the reference surface of the receiving portion. Said evacuation opening 538 is preferably larger than the drilling openings of the interchangeable templates to ease evacuation of osseous chips being formed upon drilling of the osseous structure.

In a preferred embodiment, the main implant part 301a is securely fastened to the implantation template 505 during the drilling of the tangential hole through the drilling opening 537.

It can also be provided a locking element 603 to cooperate with a corresponding recess provided in the main implant part 301a to secure the positioning of the main implant part 301a relative to the implantation template 505 during the drilling, in particular to be sure that the lateral opening provided in the main implant part 301a remains in a position facing the drilling hole 537 of the implantation template 505.

Figure 12:
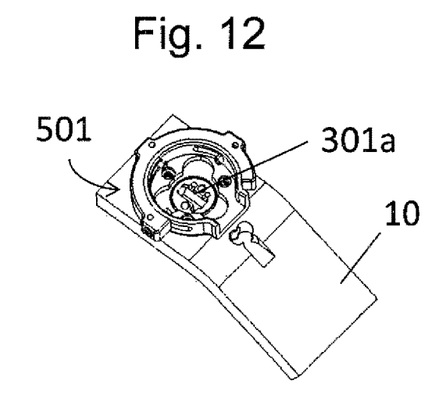

After the main implant part 301a has been positioned and implanted, and that the tangential hole corresponding to the drilling opening 537 of the implantation template 505 has been formed, the implantation template 505 is removed from the base template 501 as is illustrated in FIG. 12.

The elongated extension member 301b of the implantable device 301 can then be inserted in the tangential hole, and secured to the main implant part 301a.

In a final step as illustrated in FIG. 13, the base template 501 is removed from the osseous structure 10, leaving the implantable device 301 being totally secured within the osseous structure with a procedure that is straight forward and easy to perform. As is apparent from the above description, the proposed surgical assembly is very advantageous as it guides the surgeon during the implantation procedure and is as less as possible patient-dependent. In particular, after having positioned and fixed the base template, the surgeon can perform the subsequent steps in a very efficient and quasi-automatic manner with the use of the several drilling templates and/or implantation templates.

The invention claimed is:

1. A surgical assembly for the implantation of an implantable device in a cavity formed in an osseous structure, comprising a base template designed to be fixed to the osseous structure and a plurality of interchangeable templates intended to be successively coupled to the base template, each of the interchangeable templates having at least one through opening to be used for guiding of a tool to form the cavity in the osseous structure or for positioning of the implantable device into the cavity,
   wherein the base template comprises a receiving portion for the coupling of each one of the plurality of interchangeable templates to the base template, said receiving portion having a reference surface for specifically positioning each one of the plurality of interchangeable templates relative to the base template,
   wherein the surgical assembly further comprises a retaining element to securely fasten each of the plurality of interchangeable templates relative to the base template,
   wherein the plurality of interchangeable templates comprises at least one implantation template having at least a through implantation opening shaped for guiding the positioning of the implantable device relative to the cavity, and
   wherein the implantation template further comprises at least one through drilling opening to be used for guiding of a drilling tool to form a further hole in the osseous structure, said drilling opening being non-parallel to the implantation opening and arranged so that the hole can be drilled up to the cavity.

2. The surgical assembly of claim 1, wherein the plurality of interchangeable templates comprises at least one drilling template having at least one through drilling opening to be used for guiding of a drilling tool to form the cavity in the osseous structure.

3. The surgical assembly of claim 2, wherein the drilling template comprises a plurality of drilling openings, at least two of the drilling openings being arranged with an overlap to one another.

4. The surgical assembly of claim 2, wherein the drilling template comprises a drilling opening having a cylindrical shape with dimensions fit to guide a drilling bur.

5. The surgical assembly of claim 1, wherein said at least a through implantation opening of said at least one implantation template is shaped for guiding the positioning of the implantable device into the cavity.

6. The surgical assembly of claim 1, further comprising an implanting tool intended to be used for implanting the implantable device in the cavity with the guiding of the implantation opening.

7. The surgical assembly of claim 6, where the implanting tool comprises a first part comprising a lever for rotating the implanting tool, and a second part coupled to the first part at a first end and coupled to the implantation template on an other end, wherein the couplings are designed so that a rotation of the lever imparts a translation movement, a rotation movement, or both a rotation and translation movement of the implantable device.

8. The surgical assembly of claim 1, wherein the implantation template further comprises a locking element intended to cooperate with a corresponding recess provided in the implantable device to secure the positioning of the implantable device relative to the implantation template.

9. The surgical assembly of any one of claim 1, wherein at least one of the interchangeable templates comprises at least one complementary through opening for evacuation of osseous chips being formed upon drilling of the osseous structure.

10. The surgical assembly of claim 1, wherein the base template comprises an evacuation opening provided through the reference surface of the receiving portion, said evacuation opening being preferably larger than the through opening of the interchangeable templates to ease evacuation of osseous chips being formed upon drilling of the osseous structure.

11. The surgical assembly of claim 1, further comprising a drilling tool having at least a drilling bur, wherein said drilling bur comprises a stop element provided at a specific position along its elongated axis so as to mechanically limit penetration of the drilling bur into the osseous structure.

12. The surgical assembly of claim 1, wherein the reference surface is designed to form a surface of contact with the interchangeable template for spreading stress transmitted from the interchangeable template to the osseous structure when the cavity is formed or the implantable device is positioned in the cavity.

13. A surgical assembly for the implantation of an implantable device in a cavity formed in an osseous structure, comprising a base template designed to be fixed to the osseous structure and a plurality of interchangeable templates intended to be successively coupled to the base template, each of the interchangeable templates having at least one through opening to be used for guiding of a tool to form the cavity in the osseous structure or for positioning of the implantable device into the cavity,
wherein the base template comprises a receiving portion for the coupling of each one of the plurality of interchangeable templates to the base template, said receiving portion having a reference surface for specifically positioning each one of the plurality of interchangeable templates relative to the base template,
wherein the surgical assembly further comprises a retaining element to securely fasten each of the plurality of interchangeable templates relative to the base template,
wherein at least one of the interchangeable templates comprises a reference protrusion intended to cooperate with a surface of the cavity formed in the osseous structure to further secure positioning of said interchangeable template relative to the base template fixed in the osseous structure.

14. A surgical assembly for the implantation of an implantable device in a cavity formed in an osseous structure, comprising a base template designed to be fixed to the osseous structure and a plurality of interchangeable templates intended to be successively coupled to the base template, each of the interchangeable templates having at least one through opening to be used for guiding of a tool to form the cavity in the osseous structure or for positioning of the implantable device into the cavity,
wherein the base template comprises a receiving portion for the coupling of each one of the plurality of interchangeable templates to the base template, said receiving portion having a reference surface for specifically positioning each one of the plurality of interchangeable templates relative to the base template,
wherein the surgical assembly further comprises a retaining element to securely fasten each of the plurality of interchangeable templates relative to the base template, and
wherein the base template has a groove for receiving the retaining element, the retaining element has a protruding portion and each of the plurality of interchangeable templates comprises a recess, said protruding portion being insertable within the recess of any interchangeable template been positioned in the receiving portion of the base template in order to lock said interchangeable template relative to the base template.

15. The surgical assembly of claim 14, wherein the retaining element comprises an arc member rotatively coupled to a cylindrical portion of the base template.

16. A surgical assembly for the implantation of an implantable device in a cavity formed in an osseous structure, comprising a base template designed to be fixed to the osseous structure and a plurality of interchangeable templates intended to be successively coupled to the base template, each of the interchangeable templates having at least one through opening to be used for guiding of a tool to form the cavity in the osseous structure or for positioning of the implantable device into the cavity,
wherein the base template comprises a receiving portion for the coupling of each one of the plurality of interchangeable templates to the base template, said receiving portion having a reference surface for specifically positioning each one of the plurality of interchangeable templates relative to the base template,
wherein the surgical assembly further comprises a retaining element to securely fasten each of the plurality of interchangeable templates relative to the base template,
wherein the receiving portion of the base template comprises a cylindrical portion with a flat ring arranged at one end of said cylindrical portion to form the reference surface, and wherein the interchangeable templates comprises a cylindrical portion having dimensions to closely fit the dimensions of the cylindrical portion of the receiving portion in order to be positioned therein,
wherein the interchangeable templates further comprises an elongated portion protruding from the cylindrical portion of the interchangeable template, and
wherein the cylindrical portion of the receiving portion of the base template comprises a lateral opening to receive said elongated portion of the interchangeable template.

17. A surgical assembly for the implantation of an implantable device in a cavity formed in an osseous structure, comprising a base template designed to be fixed to the osseous structure and a plurality of interchangeable templates intended to be successively coupled to the base template, each of the interchangeable templates having at least one through opening to be used for guiding of a tool to form the cavity in the osseous structure or for positioning of the implantable device into the cavity,
wherein the base template comprises a receiving portion for the coupling of each one of the plurality of interchangeable templates to the base template, said receiving portion having a reference surface for specifically positioning each one of the plurality of interchangeable templates relative to the base template, wherein the surgical assembly further comprises a retaining element to securely fasten each of the plurality of interchangeable templates relative to the base template, wherein the surgical assembly further comprises an implanting tool intended to be used for implanting the implantable device in the cavity with the guiding of the implantation opening, and wherein the implanting tool comprises a first part comprising a lever for rotating the implanting tool, and a second part coupled to the first part at a first end and coupled to the implantation template on an other end, wherein the couplings are designed so that a rotation of the lever imparts a translation movement, a rotation movement, or both a rotation and translation movement of the implantable device.

* * * * *